US012702664B2

(12) United States Patent
Yang et al.

(10) Patent No.: US 12,702,664 B2
(45) Date of Patent: Aug. 11, 2026

(54) NICOTINIC ACID DERIVATIVE A WITH ANTI-INFLAMMATION AND ANTI-PLATELET AGGREGATION ACTIVITIES, AND USE THEREOF

(71) Applicant: Chongqing Academy of Chinese Materia Medica, Chongqing (CN)

(72) Inventors: Yong Yang, Chongqing (CN); Yanlei Guo, Chongqing (CN); Dajian Yang, Chongqing (CN)

(73) Assignee: Chongqing Academy of Chinese Materia Medica, Chongqing (CN)

( * ) Notice: Subject to any disclaimer, the term of this patent is extended or adjusted under 35 U.S.C. 154(b) by 550 days.

(21) Appl. No.: 18/029,089

(22) PCT Filed: Sep. 29, 2020

(86) PCT No.: PCT/CN2020/118818

§ 371 (c)(1),
(2) Date: Mar. 28, 2023

(87) PCT Pub. No.: WO2022/067502

PCT Pub. Date: Apr. 7, 2022

(65) Prior Publication Data

US 2023/0372323 A1 Nov. 23, 2023

(51) Int. Cl.

*A61K 31/455* (2006.01)
*A61P 7/02* (2006.01)
*A61P 29/00* (2006.01)

(52) U.S. Cl.

CPC .............. *A61K 31/455* (2013.01); *A61P 7/02* (2018.01); *A61P 29/00* (2018.01)

(58) Field of Classification Search

CPC ........ A61K 31/455; A61P 29/00; A61P 17/06; A61P 19/02; C07D 213/80

See application file for complete search history.

(56) References Cited

PUBLICATIONS

Warren et al (Org Biomol Chem, 2012; 10:4685-4688) (Year: 2012).*

J. G. Cannon, Chapter Nineteen in Burger's Medicinal Chemistry and Drug Discovery, Fifth Edition, vol. I: Principles and Practice, Wiley-Interscience 1995, pp. 783-802 (Year: 1995).*

Kim et al (Immune Netw, 2022; 22(1):e8 pp. 1-20) (Year: 2022).*

Cassotta et al (ALTEX, 2019; 37(2):223-242) (Year: 2019).*

* cited by examiner

*Primary Examiner* — Rayna Rodriguez

(74) *Attorney, Agent, or Firm* — CM Law LLP; Robert C. Klinger

(57) ABSTRACT

The present disclosure provides a nicotinic acid derivative A with an anti-inflammation activity. The nicotinic acid derivative A has a general structural formula shown in formula (I), where $R_1$ and $R_2$ are different substitution sites of a main chain, and $R_1$' and $R_2$' are different substitution sites of a side chain. In the present disclosure, the nicotinic acid derivative A has desirable anti-inflammation, anti-tumor, and anti-platelet aggregation activities, and strong selectivity, and shows a remarkable clinical application value.

(I)

1 Claim, 20 Drawing Sheets

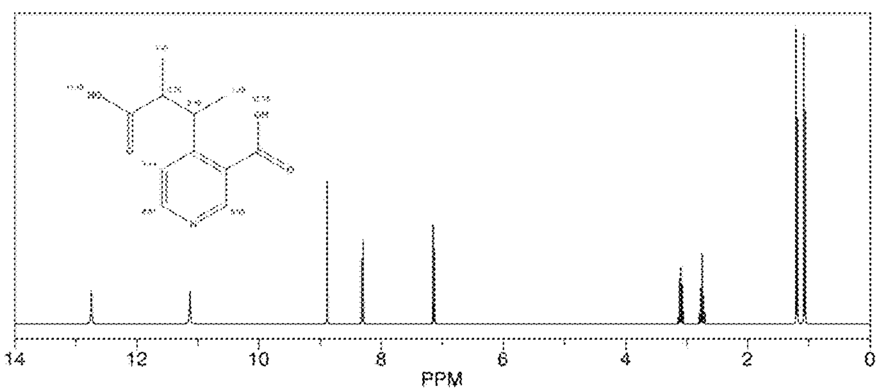

```
Protocol of the H-1 NMR Prediction (Lib=SU Solvent=DMSO 300 MHz):

Node     Shift    Base + Inc.   Comment (ppm rel. to TMS)

OH  12.75          11.00        carboxylic acid
                    1.00          1 -C*R
                    0.75          general corrections
OH  11.13          11.00        carboxylic acid
                    0.50          1 -CCC*R
                   -0.37          general corrections
CH  8.89            8.59        3-pyridine
                    0.45          1 -C=O
                    0.01          1 -C
                   -0.16          general corrections
CH  8.31            8.59        3-pyridine
                    0.20          1 -C=O
                    0.01          1 -C
                   -0.49          general corrections
CH  7.14            7.38        3-pyridine
                    0.12          1 -C=O
                   -0.10          1 -C
                   -0.26          general corrections
CH  3.10            1.50        methine
                    1.28          1 alpha -C*R
                    0.10          1 alpha -C
                    0.32          1 beta -C(=O)O
                   -0.10          1 beta -C
CH  2.75            1.50        methine
                    0.87          1 alpha -C(=O)O
                    0.10          1 alpha -C
                    0.38          1 beta -C*R
                   -0.10          1 beta -C
CH3 1.20            0.86        methyl
                    0.38          1 beta -1:C*C*C*N*C*C*1
                    0.05          1 beta -CC
                   -0.09          general corrections
CH3 1.07            0.86        methyl
                    0.23          1 beta -C(=O)O
                    0.05          1 beta -CC
                   -0.07          general corrections

1H NMR Coupling Constant Prediction

shift   atom index  coupling partner, constant and vector

12.75        1
11.13        4
8.89        11
                    13   0.4  H-C*N*C-H
8.31        13
                     3   7.5  H-C*C-H
                    11   0.4  H-C*N*C-H
7.14         3
                    13   7.5  H-C*C-H
3.10         9
                     7   7.0  H-C-C-H
                    14   6.8  H-C-CH2-H
2.75         7
                     9   7.0  H-C-C-H
                    16   6.8  H-C-CH2-H
1.20        14
                     9   6.8  H-CH2-C-H
1.07        16
                     7   6.8  H-CH2-C-H
```

FIG. 2

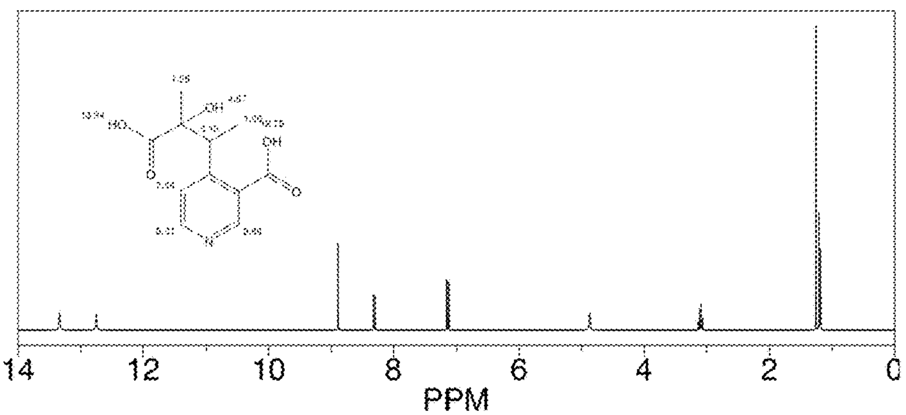

```
Protocol of the H-1 NMR Prediction (Lib=SU Solvent=DMSO 300 MHz):

Node     Shift    Base + Inc.   Comment (ppm rel. to TMS)

OH  12.75          11.00        carboxylic acid
                    1.00          1 -C*R
                    0.75          general corrections
OH  13.34          11.00        carboxylic acid
                    0.50          1 -CCC*R
                    1.84          general corrections
OH  4.87            4.20        alcohol
                    0.85          1 -CCC*R
                   -0.18          general corrections
CH  8.89            8.59        3-pyridine
                    0.49          1 -C=O
                    0.01          1 -C
                   -0.16          general corrections
CH  8.31            8.59        3-pyridine
                    0.20          1 -C=O
                    0.01          1 -C
                   -0.49          general corrections
CH  7.14            7.38        3-pyridine
                    0.12          1 -C=O
                   -0.10          1 -C
                   -0.26          general corrections
CH  3.10            1.50        methine
                    1.28          1 alpha -C*R
                    0.10          1 alpha -C
                    0.00          1 beta -O
                    0.32          1 beta -C(=O)O
                   -0.10          1 beta -C
CH3 1.26            0.86        methyl
                    0.25          1 beta -O
                    0.23          1 beta -C(=O)O
                    0.05          1 beta -CC
                   -0.13          general corrections
CH3 1.20            0.86        methyl
                    0.38          1 beta -1:C*C*C*N*C*C*1
                    0.05          1 beta -CC
                   -0.09          general corrections

1H NMR Coupling Constant Prediction

shift   atom index  coupling partner, constant and vector

12.75        1
13.34        4
4.87        17
8.89        11
                   13   0.4  H-C*N*C-H
8.31        13
                    3   7.5  H-C*C-H
                   11   0.4  H-C*N*C-H
7.14         3
                   13   7.5  H-C*C-H
3.10         9
                   14   6.8  H-C-CH2-H
1.26        15
1.20        14
                    9   6.8  H-CH2-C-H
```

FIG. 4

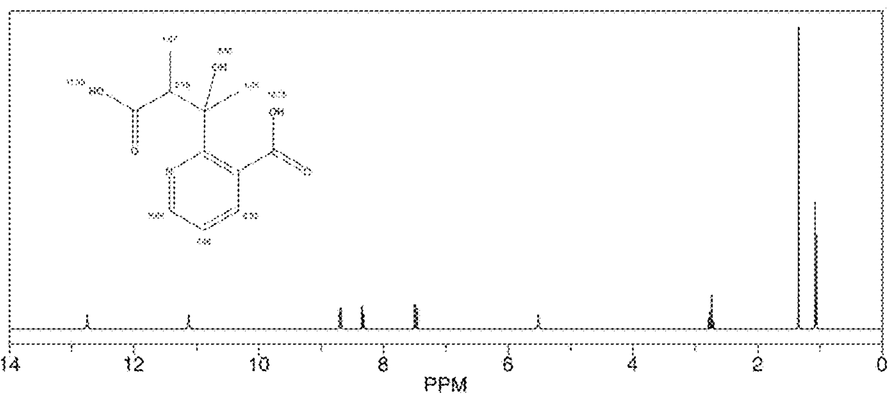

Protocol of the H-1 NMR Prediction (Lib=SU Solvent=DMSO 300 MHz):

| Node | Shift | Base + Inc. | Comment (ppm rel. to TMS) |
|---|---|---|---|
| OH | 12.75 | 11.00 | carboxylic acid |
| | | 1.00 | 1 -C*R |
| | | 0.75 | general corrections |
| OH | 11.13 | 11.00 | carboxylic acid |
| | | 0.50 | 1 -CCC*R |
| | | -0.37 | general corrections |
| OH | 5.52 | 4.20 | alcohol |
| | | 1.10 | 1 -C-C*R |
| | | 0.22 | general corrections |
| CH | 8.69 | 8.59 | 2-pyridine |
| | | 0.06 | 1 -C-O |
| | | 0.20 | 1 -C=O |
| | | -0.16 | general corrections |
| CH | 7.48 | 7.38 | 2-pyridine |
| | | 0.02 | 1 -C-O |
| | | 0.12 | 1 -C=O |
| | | -0.04 | general corrections |
| CH | 8.33 | 7.75 | 2-pyridine |
| | | 0.30 | 1 -C-O |
| | | 0.42 | 1 -C=O |
| | | -0.14 | general corrections |
| CH | 2.75 | 1.50 | methine |
| | | 0.87 | 1 alpha -C(=O)O |
| | | 0.10 | 1 alpha -C |
| | | 0.38 | 1 beta -C*R |
| | | 0.00 | 1 beta -O |
| | | -0.10 | 1 beta -C |
| CH3 | 1.35 | 0.86 | methyl |
| | | 0.38 | 1 beta -1:C*N*C*C*C*C*1 |
| | | 0.25 | 1 beta -O |
| | | 0.05 | 1 beta -CC |
| | | -0.19 | general corrections |
| CH3 | 1.07 | 0.86 | methyl |
| | | 0.23 | 1 beta -C(=O)O |
| | | 0.05 | 1 beta -CC |
| | | -0.07 | general corrections |

1H NMR Coupling Constant Prediction

| shift | atom index | coupling partner, constant and vector | | |
|---|---|---|---|---|
| 12.75 | 1 | | | |
| 11.13 | 4 | | | |
| 5.52 | 17 | | | |
| 8.69 | 13 | | | |
| | | 12 | 7.5 | H-C*C-H |
| | | 11 | 1.5 | H-C*CH*C-H |
| 7.48 | 12 | | | |
| | | 13 | 7.5 | H-C*C-H |
| | | 11 | 7.5 | H-C*C-H |
| 8.33 | 11 | | | |
| | | 12 | 7.5 | H-C*C-H |
| | | 13 | 1.5 | H-C*CH*C-H |
| 2.75 | 7 | | | |
| | | 15 | 6.8 | H-C-CH2-H |
| 1.35 | 14 | | | |
| 1.07 | 15 | | | |
| | | 7 | 6.8 | H-CH2-C-H |

FIG. 6

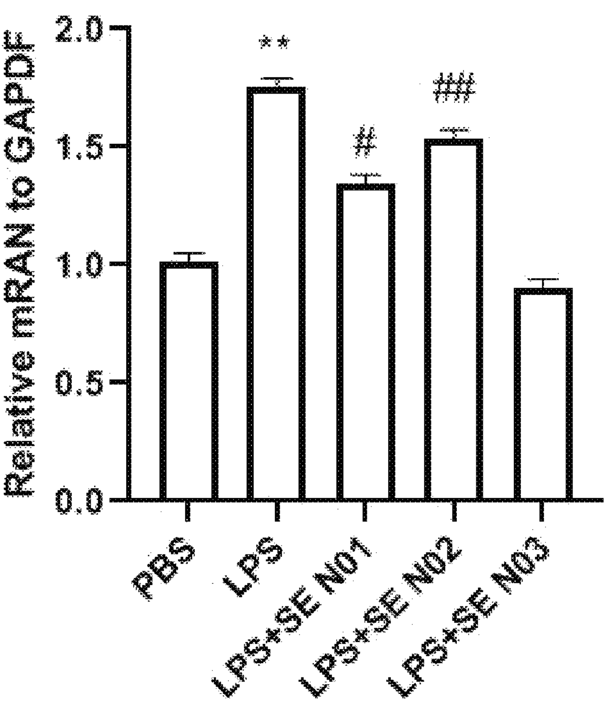
FIG. 7A
IL-8
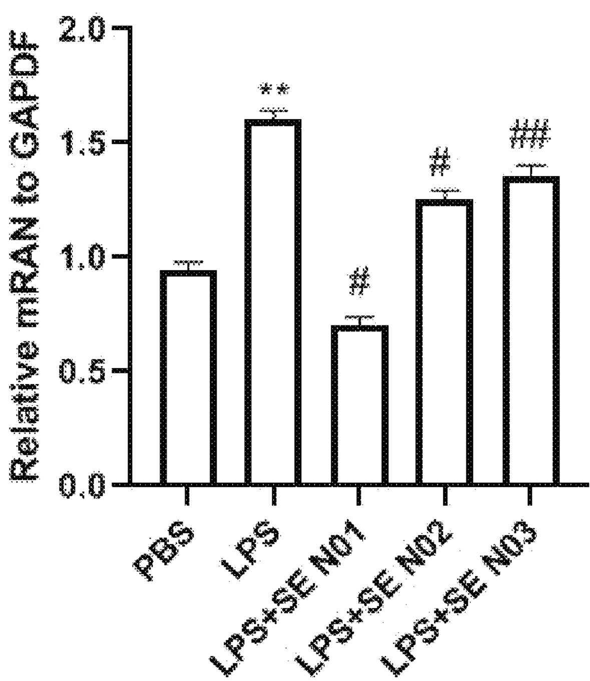
FIG. 7B

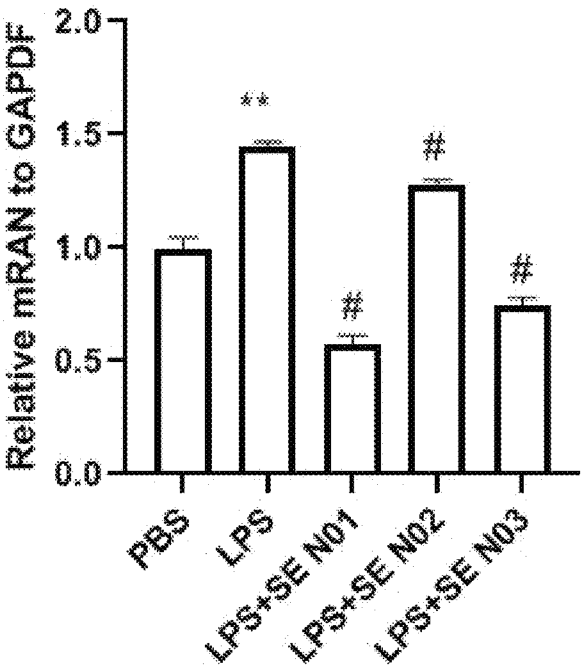
FIG. 7E
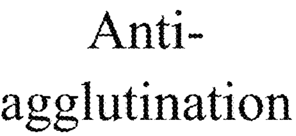
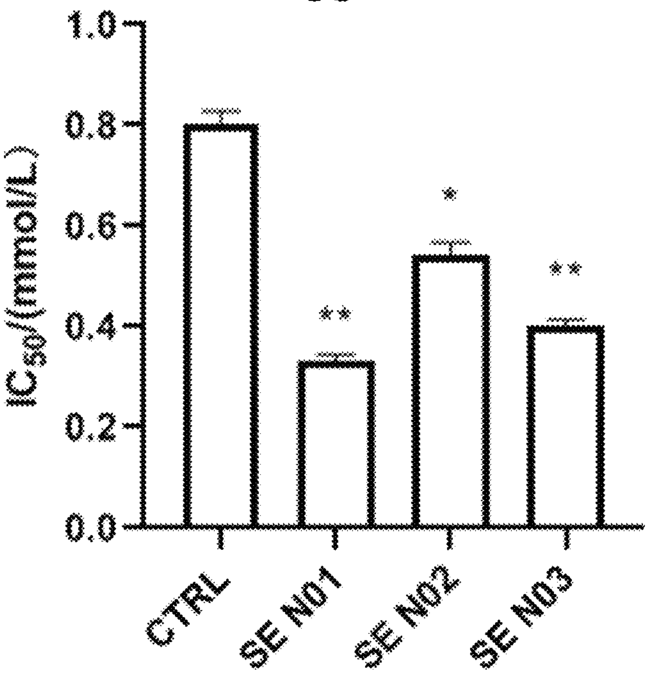
FIG. 8

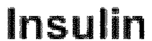
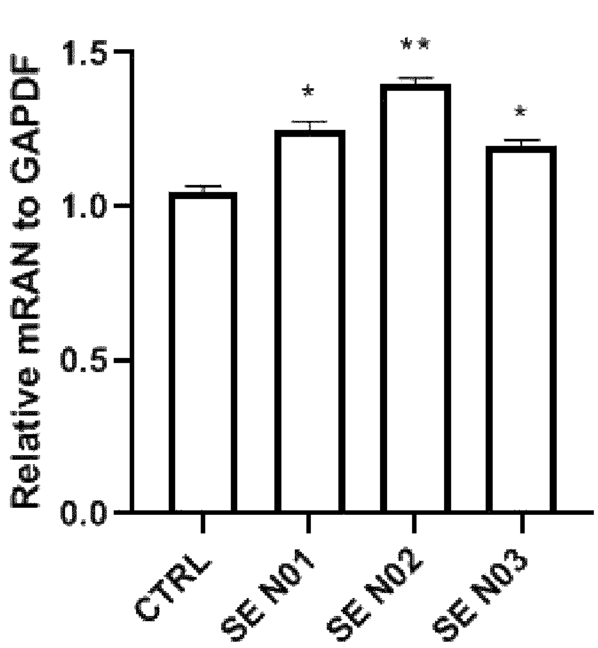
FIG. 9C
G6pase
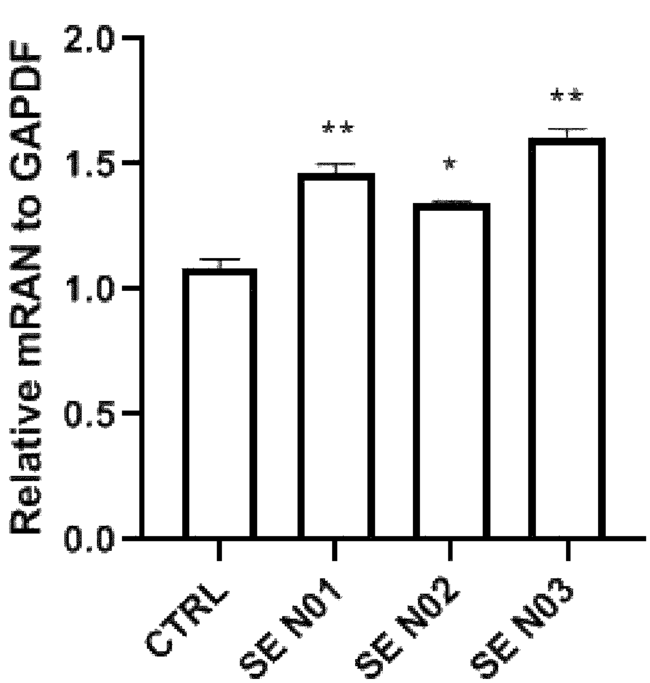
FIG. 9D

NICOTINIC ACID DERIVATIVE A WITH ANTI-INFLAMMATION AND ANTI-PLATELET AGGREGATION ACTIVITIES, AND USE THEREOF

CROSS-REFERENCE TO RELATED APPLICATION

This patent application is a National Stage entry of Patent Cooperation Treaty Application No. PCT/CN2020/118818 filed Sep. 29, 2020, the disclosure of which is incorporated by reference herein in its entirety as part of the present application.

TECHNICAL FIELD

The present disclosure relates to a compound, more specifically to a nicotinic acid derivative A with anti-inflammation and anti-platelet aggregation activities, and use thereof. The nicotinic acid derivative A is isolated from the extraction of a *Tripterygium* genus-derived medicinal material.

BACKGROUND

During the long-term clinical diagnosis and treatment of traditional Chinese medicine, plants of *Tripterygium* genus, Celastraceae have been used for the treatment of rheumatic arthralgia with a long history. These plants are bitter, cold, and poisonous, and have the effects of dispelling wind and eliminating dampness, relaxing tendons and activating collaterals, as well as clearing away heat and toxic materials. Moreover, these plants can also be used as a clinically important immunosuppressant, and plays an important role in the treatment of autoimmune diseases such as rheumatoid arthritis, primary nephrotic syndrome, and systemic lupus erythematosus.

*Tripterygium* plants mainly include *Tripterygium hypoglaucum* (Levl.) Hutch, *Tripterygium regelii* Sprague et Takeda, and *Tripterygium wilfordii* Hook. f According to statistics from the official website of the National Medical Products Administration, there are currently 45 related preparations of *Tripterygium* genus-derived medicinal materials from 43 domestic drug manufacturers on the market in China. The chemical components of *Tripterygium* genus mainly include sesquiterpene alkaloids, diterpenes, and triterpenes. Among them, the total alkaloids of *Tripterygium wilfordii* account for about 0.07% to 0.29%, and these components play an important role in the immunosuppression. The sesquiterpene alkaloid is a dihydrofuran-typed sesquiterpene. The reported structures of the sesquiterpene alkaloid mainly include a total of 71 types in wilfordate/evoninate, hydroxy-wilfordate/evoninate, and iso-wilfordate/evoninate. *Tripterygium*-derived sesquiterpene alkaloids are a class of sesquiterpenes with high oxygen content. These sesquiterpenes contain a special macrocyclic dilactone skeleton structure, including two moieties of 2-(carboxyalkyl) nicotinic acid and polyoxygenated dihydro-β-agarofuran sesquiterpenoid. The hydroxyl groups of the polyoxygenated dihydro-β-agarofuran sesquiterpenoid moiety are typically esterified with various organic acids, including acetic acid, benzoic acid, furanic acid, nicotinic acid, and fatty acids. The 2-(carboxyalkyl) nicotinic acid moiety is mainly derived from alkyne acid, vitamin acid, hydroxyvitamin acid, or their homologues. Meanwhile, the difference in the 2-(carboxyalkyl) nicotinic acid moiety is a core of the difference in the macrocyclic dilactone skeleton structure, and also a core of the structural diversity of the chemical components of the *Tripterygium*-derived alkaloids.

During the long-term clinical diagnosis and treatment of traditional Chinese medicine, it is discovered that plants of *Tripterygium* genus, Celastraceae have been used for the treatment of rheumatic arthralgia with a definite effect. These plants are bitter, cold, and poisonous, and have the effects of dispelling wind and eliminating dampness, relaxing tendons and activating collaterals, as well as clearing away heat and toxic materials. Moreover, these plants play an important role in the treatment of autoimmune diseases such as rheumatoid arthritis. The mechanism of *Tripterygium* genus-derived medicinal materials in treating rheumatoid arthritis is closely related to the key targets of inflammation generation and T-cell immune regulation. After one week of rheumatoid arthritis treatment, the *Tripterygium hypoglaucum* has an obvious inhibitory effect on the secondary paw swelling and arthritis indexes of model rats with adjuvant arthritis. The *Tripterygium hypoglaucum* has a significant effect on reducing the concentration of pro-inflammatory factors IL-1α and IL-1β, as well as a functional protein MMP3 in serum, and shows a significant effect on increasing the concentration of anti-inflammatory factors IL-4 and IL-10 in serum. After three weeks of administration, the proportion of regulatory T cells (Tregs) in T lymphocytes is significantly higher than that of a model group, indicating an evident therapeutic effect. In-depth and systematic exploration was conducted on the researches of immunosuppressive active ingredients in the *Tripterygium* genus-derived medicinal materials. These researches had successively invested more than 15 million yuan in national or provincial scientific research projects. Relevant topics included: the Ministry of Science and Technology (MOST), the Special Project of National Major New Drug Creation Technology: "New Drug Research of Haoteng Qufeng Capsules for Rheumatoid Treatment" (project number: 2017ZX09101002-002-004); the Project of Chongqing Municipal Health Bureau: "Study on the relationships between hemolysin antibody inhibition efficacy and administration doses and time of Huobahua root tablets" (project number: cstc2013jcsf10011); the Project of Chongqing Science and Technology Bureau: "Promotion and improvement of industrialization of large varieties of Huobahua root tablets" (project number: cstc2014jcsf10001); the Project of Chongqing Municipal Science and Technology Bureau: "Study on the mechanism of action of Huobahua root tablets in the immunosuppression of rheumatoid arthritis based on metabolomics of traditional Chinese medicine" (project number: 2015cstc-jbky-01913); and the Project of Chongqing Science and Technology Bureau: "Study on the metabolic kinetics of wilforine in Beagle dogs" (project number: cstc2018jxjl130055).

SUMMARY

On the basis of problems in the prior art, the present disclosure provides a nicotinic acid derivative A with anti-inflammation and anti-platelet aggregation activities, having a general structural formula as follows:

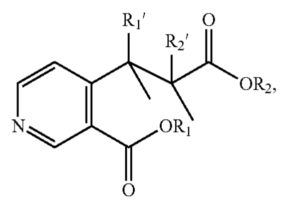

where $R_1$ and $R_2$ are different substitution sites of a main chain, and $R_1$' and $R_2$' are different substitution sites of a side chain.

Further, the $R_1$ is substituted with a substituent selected from the group consisting of $H^+$, $OH^-$, $CH_3^-$, SH, $CH_2CH_3^-$, $CONH_2^-$, and $NH_2^-$; the $R_2$ is substituted with a substituent selected from the group consisting of $H^+$, $OH^-$, $CH_3^-$, SH, $CH_2CH_3^-$, $CONH_2^-$, and $NH_2^-$; and the substitution sites of the $R_1$ and the $R_2$ are capable of being simultaneously substituted by the substituents.

Further, the $R_1$' is substituted with a substituent selected from the group consisting of $H^+$, $OH^-$, and $CH_3^-$; the $R_2$' is substituted with a substituent selected from the group consisting of $H^+$, $OH^-$, and $CH_3^-$; and the substitution sites of the $R_1$' and the $R_2$' are capable of being simultaneously substituted by the substituents.

Further, the nicotinic acid derivative A has a structural formula as follows:

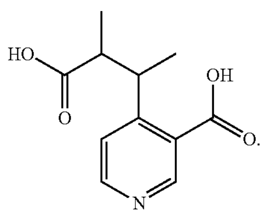 [SMILES: CC(C(=O)O)C(C)c1ccncc1C(=O)O]

Further, the nicotinic acid derivative A has a structural formula as follows:

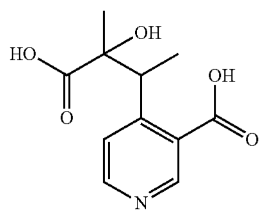 [SMILES: CC(c1ccncc1C(=O)O)C(C)(O)C(=O)O]

Further, the nicotinic acid derivative A has a structural formula as follows:

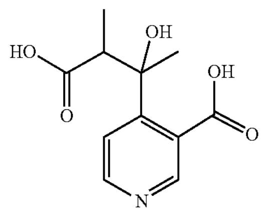 [SMILES: CC(C(=O)O)C(C)(O)c1ccncc1C(=O)O]

The present disclosure provides use of the nicotinic acid derivative A with an anti-inflammation activity of *Tripterygium* in preparation of an anti-inflammatory drug.

The present disclosure provides use of the nicotinic acid derivative A with an anti-platelet aggregation activity of *Tripterygium* in preparation of an anti-platelet aggregation drug.

The present disclosure provides use of the nicotinic acid derivative A with an anti-tumor activity of *Tripterygium* in preparation of an anti-tumor drug.

The beneficial technical effects of the present disclosure include: in the present disclosure, the nicotinic acid derivative A has desirable anti-inflammation, anti-tumor, and anti-platelet aggregation activities, and has strong selectivity, which shows a remarkable clinical application value.

BRIEF DESCRIPTION OF THE DRAWINGS

FIG. 2 shows a $^1$H-NMR spectrum of the nicotinic acid derivative A-1;

FIG. 4 shows a $^1$H-NMR spectrum of the nicotinic acid derivative A-2;

FIG. 6 shows a $^1$H-NMR spectrum of the nicotinic acid derivative A-3;

FIGS. 7A-E show an anti-inflammation activity of the nicotinic acid derivative A;

FIG. 8 shows an anti-platelet aggregation activity of the nicotinic acid derivative A;

FIGS. 9A-E show a hypoglycemic activity of the nicotinic acid derivative A;

DETAILED DESCRIPTION OF THE EMBODIMENTS

Figure 1:
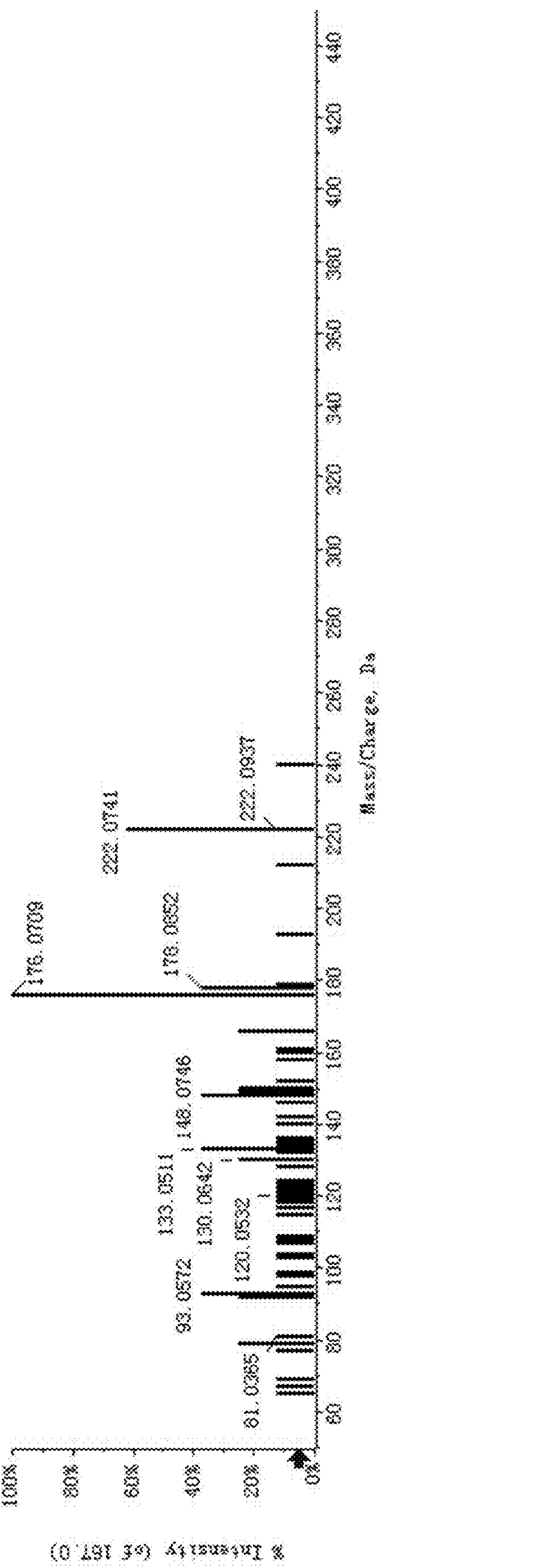
FIG. 1 shows an electrospray ionization-mass spectrometry (ESI-MS) spectrum of a nicotinic acid derivative A-1.

Example 1 Preparation Method of a Nicotinic Acid Derivative A

A root bark of *Tripterygium hypoglaucum* was crushed to obtain a medicinal material powder. 1 Kg of the medicinal material powder was placed in a 5,000 mL round-bottomed flask, soaked with 3,000 mL and 2,000 mL of water for 60 min separately, and then extracted under reflux for 60 min separately. Two obtained extracting solutions were combined and concentrated into an extract, the extract was diluted with a small amount of water, and then extracted with 1.5 times, 1 time, and 0.5 times of ethyl acetate separately. (1) The ethyl acetate layers were combined and an organic phase was recovered. A resulting extract was evaporated to dryness, and 5 g of the extract was dissolved in 7.5 mL of pure methanol, added with 2.5 mL of a 0.4 mol/L NaOH methanol solution, and then reacted in a water bath at 60° C. for 4 h. A reaction solution was evaporated to remove the methanol, diluted with 10 mL of water, and extracted 3 times with 2 times the amount of ethyl acetate. An aqueous layer was evaporated to dryness. The aqueous layer was wet-loaded and passed through a C18 column, eluted with a 5% methanol aqueous solution at a natural flow rate. The eluates were intercepted in sections, and components of each eluate were monitored by LC-MS. (2) The aqueous layer was concentrated into an extract, dissolved with a small amount of water, and the passed through a polyamide column. A resulting product was rinsed with 5 times the column volume of water, and an eluate was collected and evaporated to dryness. A resulting product was re-dissolved with a small amount of water, added 3 times the amount of 95% ethanol and stirred for 30 min, centrifuged to obtain a supernatant, and evaporated to dryness. An obtained product was dissolved in 5% methanol and separated by preparative liquid phase, and then eluted with a 15% methanol aqueous solution serving as a mobile phase. The eluates were collected in sections, and components of each eluate were monitored by LC-MS.

Example 2 Preparation Method of a Nicotinic Acid Derivative A

A root bark of *Tripterygium hypoglaucum* was crushed to obtain a medicinal material powder. 1 Kg of the medicinal material powder was placed in a 5,000 mL round-bottomed flask, soaked with 3,000 mL and 2,000 mL of an 80% ethanol solution for 60 min separately, and then extracted under reflux for 60 min separately, and a pH value was adjusted to 4.0. Two obtained extracting solutions were combined and the ethanol was recovered, an extract was diluted with a small amount of water, and then extracted with 1.5 times, 1 time, and 0.5 times of ethyl acetate separately. The ethyl acetate layers were combined and an organic phase was recovered. A resulting extract was evaporated to dryness, and 5 g of the extract was dissolved in 7.5 mL of pure methanol, added with 2.5 mL of a 0.4 mol/L NaOH methanol solution, and then reacted in a water bath at 60° C. for 4 h. A reaction solution was evaporated to remove the methanol, diluted with 10 mL of water, and extracted 3 times with 2 times the amount of ethyl acetate. An aqueous layer was evaporated to dryness. The aqueous layer was wet-loaded and passed through a C18 column, eluted with a 5% methanol aqueous solution at a natural flow rate. The eluates were intercepted in sections, and components of each eluate were monitored by LC-MS. A monomer was obtained by preparative liquid phase separation.

Figure 3:
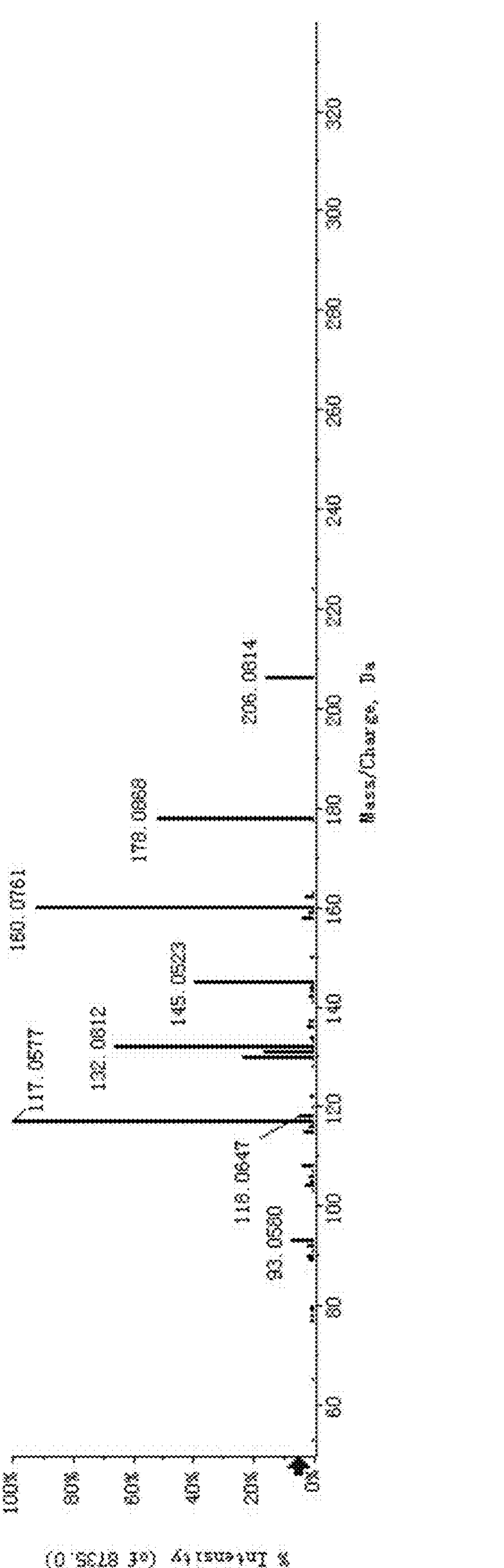
FIG. 3 shows an ESI-MS spectrum of a nicotinic acid derivative A-2.
Figure 5:
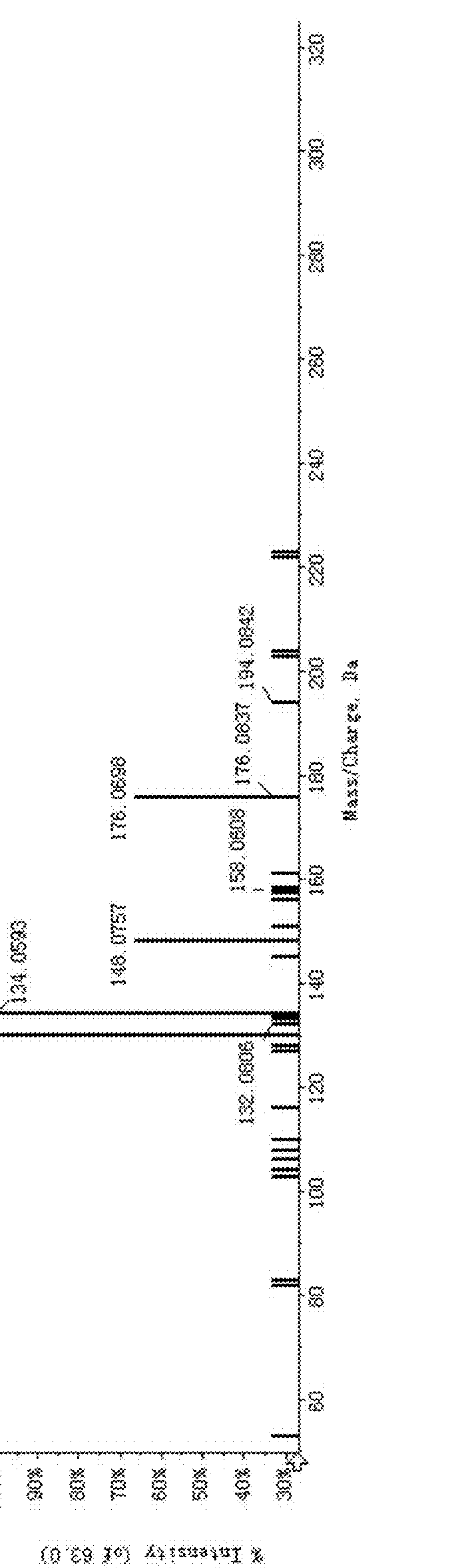
FIG. 5 shows an ESI-MS spectrum of a nicotinic acid derivative A-3.

The $^1$H-NMR chemical structure analysis and ESI-MS chemical structure analysis were conducted on the class-I nicotinic acid derivatives. The specific results were shown in Table 1, Table 2 and FIG. 1, FIG. 2, FIG. 3, FIG. 4, FIG. 5, and FIG. 6.

TABLE 1

$^1$H-NMR structure analysis of nicotinic acid derivatives

| Name | $^1$H-NMR: (TMS, $D_2O$, 500 MHz) |
|---|---|
| Nicotinic acid derivative A-1 | $^1$H NMR (500 MHz, $D_2O$) δ 8.89 (s, 1H), 8.31 (d, J = 7.5 Hz, 1H), 7.14 (d, J = 7.5 Hz, 1H), 3.31 (t, J = 7.1 Hz, 2H), 2.37 (q, J = 7.0 Hz, 6.8 Hz, 1H), 1.84(q, J = 7.1 Hz, 7.0 Hz, 2H), 1.07 (d, J = 6.8 Hz, 3H). |
| Nicotinic acid derivative A-2 | $^1$H NMR (500 MHz, $D_2O$) δ 8.89 (s, 1H), 8.31 (d, J = 7.5 Hz, 1H), 7.14 (d, J = 7.5 Hz, 1H), 3.31 (t, J = 7.1 Hz, 2H), 1.99(t, J = 7.1 Hz, 2H), 1.26 (d, J = 7.1 Hz, 3H). |
| Nicotinic acid derivative A-3 | $^1$H NMR (500 MHz, $D_2O$) δ 8.89 (s, 1H), 8.31 (d, J = 7.5 Hz, 1H), 7.14 (d, J = 7.5 Hz, 1H), 3.25(q, J = 7.5 Hz, 2H), 2.30 (m, J = 7.0 Hz, J = 7.0 Hz, J = 6.8 Hz, H), 2.12 (t, J = 7.0 Hz3H), 4.74(s, H)). |

The nicotinic acid derivatives were subjected to ESI-MS chemical structure analysis. The results were specifically shown in Table 2:

TABLE 2

ESI-MS structure analysis of nicotinic acid derivatives

| Name | Triple-Tof high-resolution mass spectrometry (ESI_Positive) |
|---|---|
| Nicotinic acid derivative A-1 | ESI-Positive (Triple-Tof 4600) [M + H]+: 224.0914 206.0812, 178.0860, 150.0548, 124.0391, 106.0649, 80.0497 |
| Nicotinic acid derivative A-2 | ESI-Positive (Triple-Tof 4600) [M + H]+: 240.0863 222.0759, 204.0652, 194.0807, 176.0702, 158.0596, 134.0595, 130.0646, 117.0572, 106.0652, 77.0388 |
| Nicotinic acid derivative A-3 | ESI-Positive (Triple-Tof 4600) [M + H]+: 224.0914 206.0812, 178.0860, 150.0548, 124.0391, 106.0649, 80.0497 |

Example 3 Investigation of an Anti-Inflammation Activity of the Nicotinic Acid Derivative A Subculture: macrophages were subcultured in a DMEM medium containing 10% FBS and 1% double antibody in an incubator at 37° C. and 5% $CO_2$. About $1\times10^7$ cells were collected, added with a cell lysate (including Tris at pH=7.4, 150 mmol/L NaCl, 1% NP-40, and cocktail protease inhibitor), treated in an ice bath for 30 min, centrifuged at 4° C. and 12,000 r/min for 20 min. A supernatant was collected for storage.

Drug intervention: macrophages were subcultured in a DMEM medium containing 10% FBS and 1% double antibody in an incubator at 37° C. and 5% C02. About $1\times10^7$ cells were collected. Grouping: there were a control PBS group, a tested molecule group, and a tested molecule+PBS group. The final concentrations of the molecules obtained in Example 2 to be tested were determined according to specific experiments.

Figure 7C:
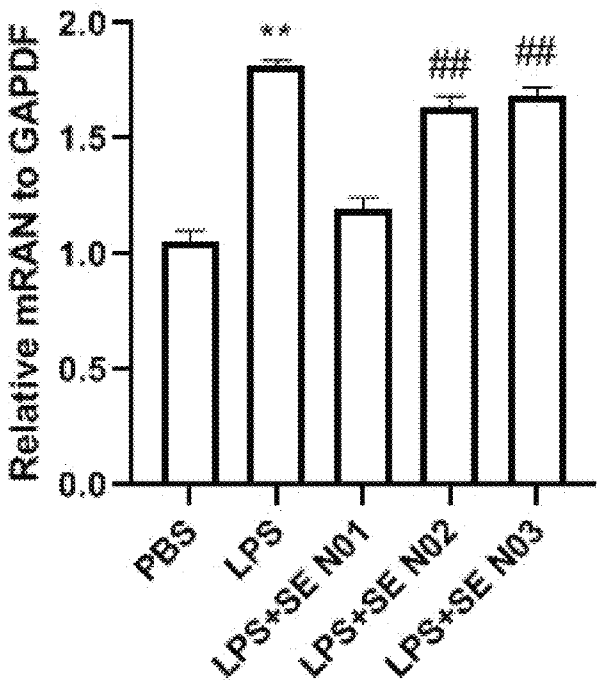
Figure 7D:
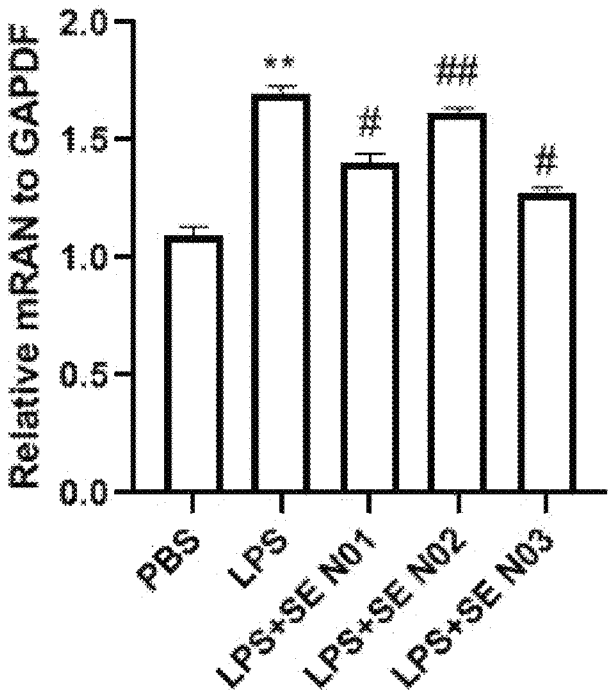

Based on the grouping, after the macrophages were pretreated with different alkaloid molecules for 12 h, the following experiments were conducted: (1) RT-PCR analysis was conducted to detect the transcriptional expression changes of inflammatory factors (IL-6, IL-8, MCP-1, and TNF-α) and transcription regulators (PPART) in the cells of each experimental group. The experimental results are shown in FIGS. 7A-E.

Example 4 Investigation of an Anti-Platelet Aggregation Activity of the Nicotinic Acid Derivative A An inhibitory activity of a target compound on adenosine diphosphate (ADP)-induced platelet aggregation in rabbits was tested by a Born's nephelometric method. Blood was collected from the heart of rabbits and preliminarily mixed with 3.8% sodium citrate at 1:9. A part of the blood was centrifuged at 1,000 r/min for 10 min to prepare platelet-rich plasma (PRP). The remaining part of the blood was centrifuged at 3,000 r/min for 15 min to prepare platelet poor plasma (PPP). The platelet aggregation activity was tested by the turbidimetric method. 280 μL of the PRP and 10 μL of test compounds with different concentrations (1,000 μmol/L, 500 μmol/L, 200 μmol/L, 100 μmol/L, and 10 μmol/L) were added into an assay tube, and warm-incubate for 5 min. 10 μL of ADP (at a final concentration of 10 μmol/L) was added as an inducer, and a maximum platelet aggregation rate within 5 min was observed and recorded.

Each concentration was measured in parallel. The experimental results are shown in FIG. 8.

Figure 9A:
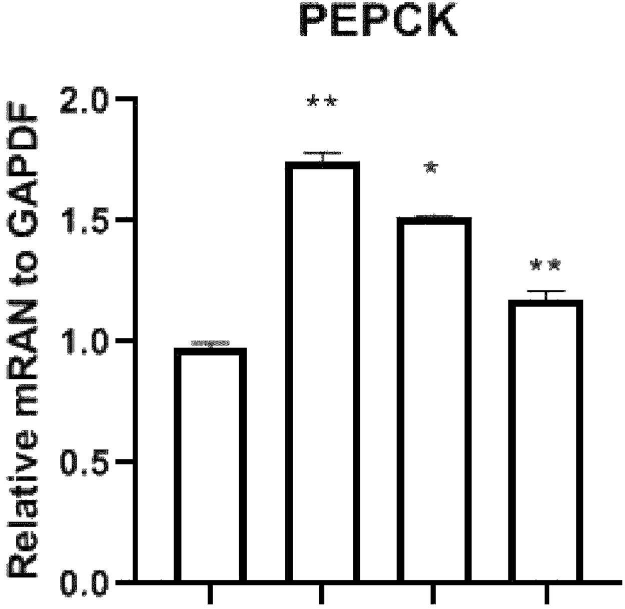
Figure 9B:
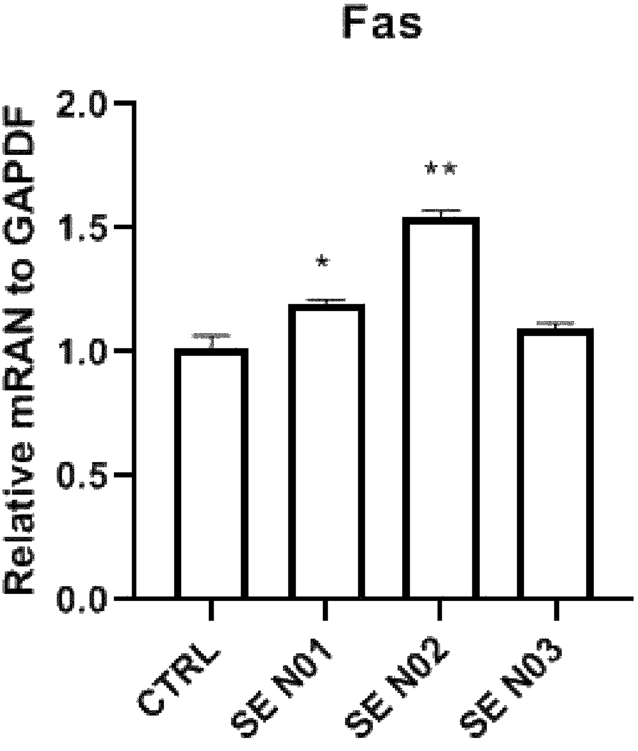
Figure 9E:
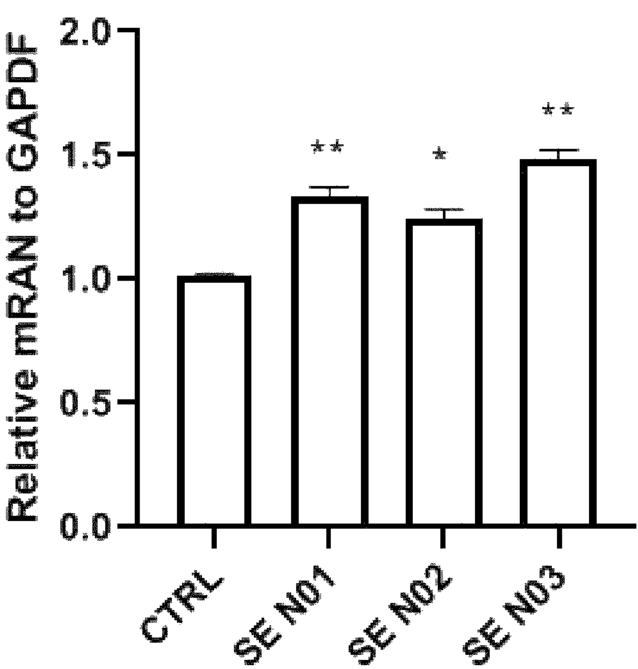

Example 5 Investigation of a Hypoglycemic Activity of the Nicotinic Acid Derivative A HepG2 cells were subcultured in a six-well plate and divided into 4 groups: a control PBS group, a high glucose model group, a high glucose model+tested molecule group, and a tested molecule+PBS group. The cells were cultured for 12 h after drug administration to extract cellular RNA, and subjected to reverse transcription. The RT-PCR was conducted to detect changes in the transcriptional expression levels of inflammatory factors (IL-6, IL-8, MCP-1, and TNF-α) and transcriptional regulators (PPART) in the cells of each experimental group. The experimental results were shown in FIGS. 9A-E.

Figure 10A:
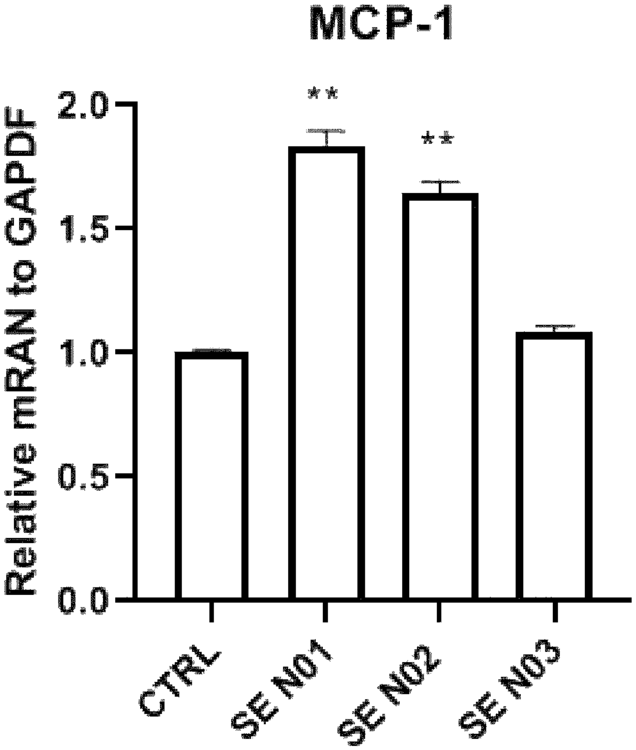
FIGS. 10A-F show an anti-hepatoma cell activity of the nicotinic acid derivative A.
Figure 10B:
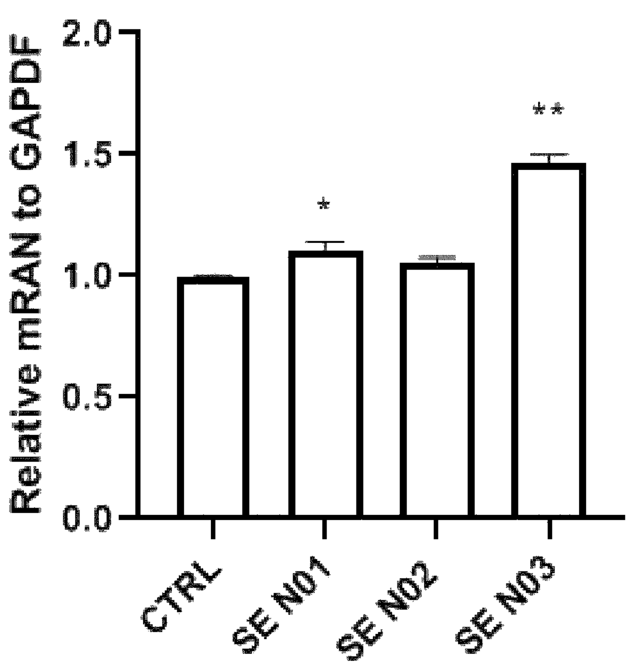
Figure 10C:
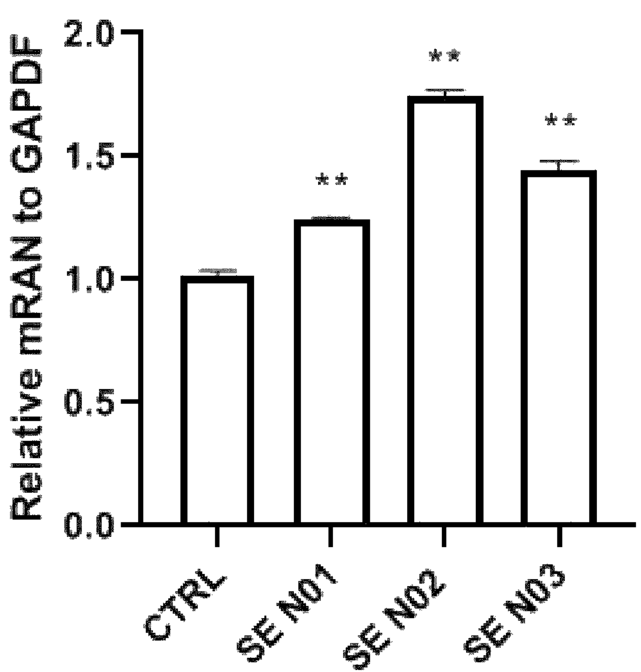
Figure 10D:
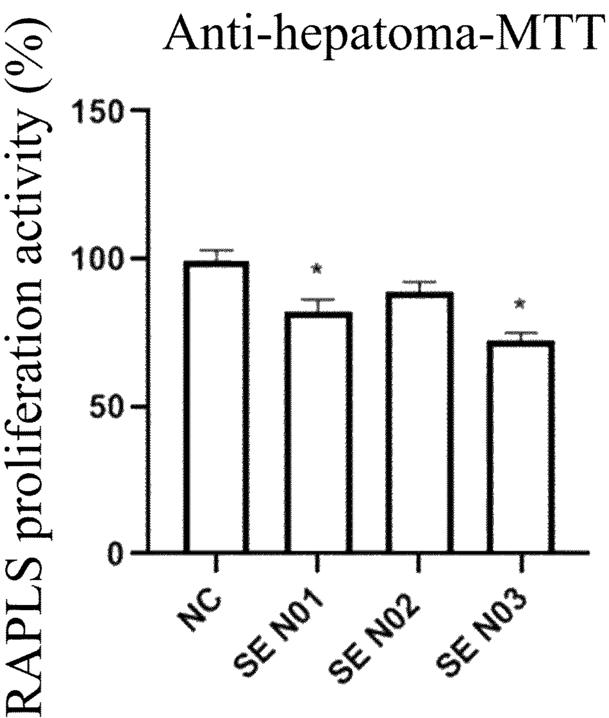
Figure 10E:
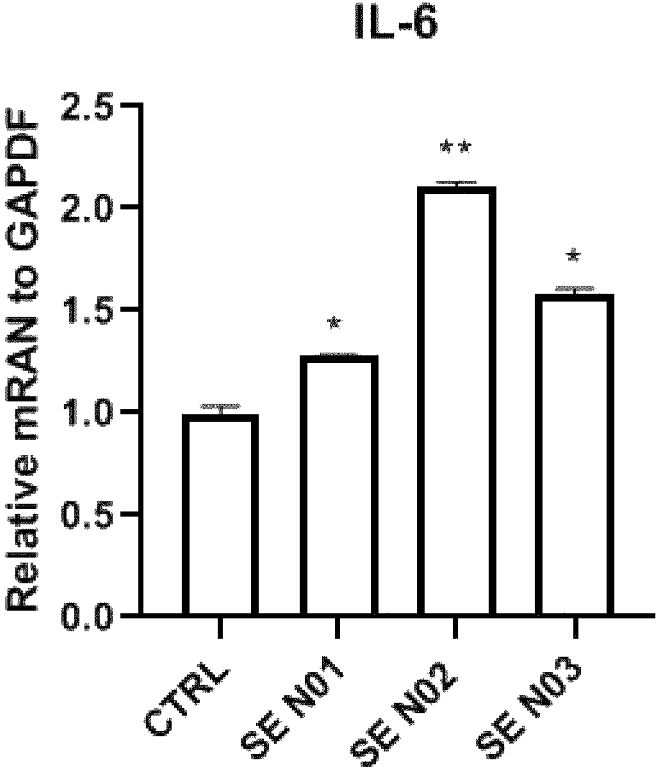
Figure 10F:
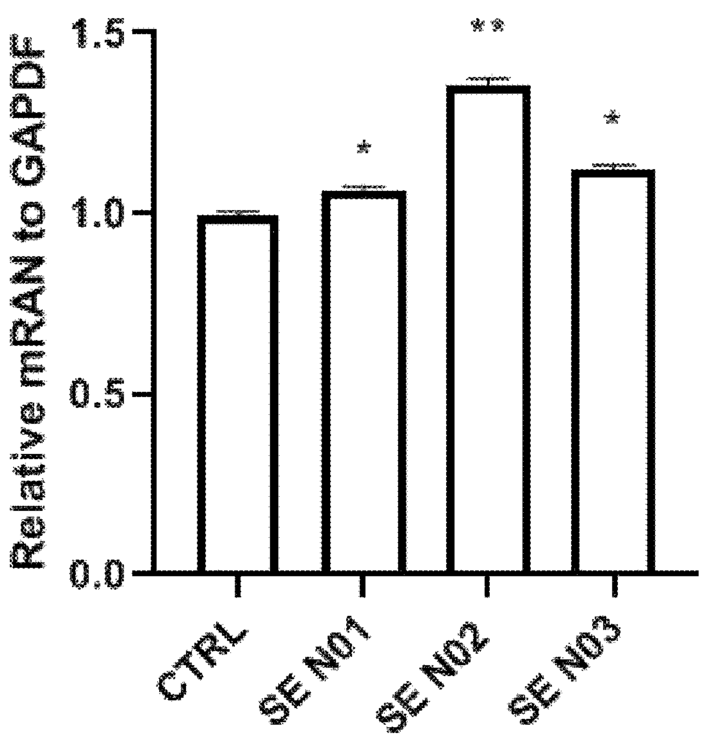

Example 6 Investigation of an Anti-Hepatoma Cell Activity of the Nicotinic Acid Derivative A (1) Drug concentration toxicity test: HepG2 cells were cultured in a DMEM medium containing 10% FBS and 1% double antibody in an incubator at 37° C. and 5% $CO_2$. The logarithmic-phase cells were collected, a concentration of a cell suspension was adjusted, and the cell suspension was divided into a 96-well plate, at 150 μL per well. After culturing for 24 h, 200 L of the samples to be tested at different concentrations were added, and the culture was continued until a required time. A supernatant was discarded, 80 μL of a fresh culture medium was added, and then 20 μL of an MTT solution was added, and the culture was continued for 3 h. A supernatant was discarded, and 100 μL of dimethyl sulfoxide was added to each well, the plate was placed on a shaker and shaken at a low speed for 10 min, and an absorbance value of each well was measured at 570 mm to calculate the cell viability. Detection of anti-hepatoma activity: HepG2 cells were subcultured in a six-well plate and divided into 3 groups: a control PBS group, a tested molecule group, and a tested molecule+PBS group. The cells were cultured for 12 h after drug administration to extract cellular RNA, and subjected to reverse transcription. The RT-PCR was conducted to detect changes in the transcriptional expression levels of inflammatory factors (IL-6, IL-8, MCP-1, and TNF-α) and transcriptional regulators (PPART) in the cells of each experimental group. The experimental results were shown in FIGS. 10A-F.

Example 7 Analysis for Molecular Docking of the Nicotinic Acid Derivative A

Reverse docking targets were collected from the following three sources: DisGeNET database (https://www.disgenet.org/, v6), Online Mendelian Inheritance in Man (OMIM) database (http://www.omim.org/, updated on Jun. 26, 2020), and GeneCards database (https://www.genecards.org/, updated on Mar. 11, 2020).

Figure 11A:
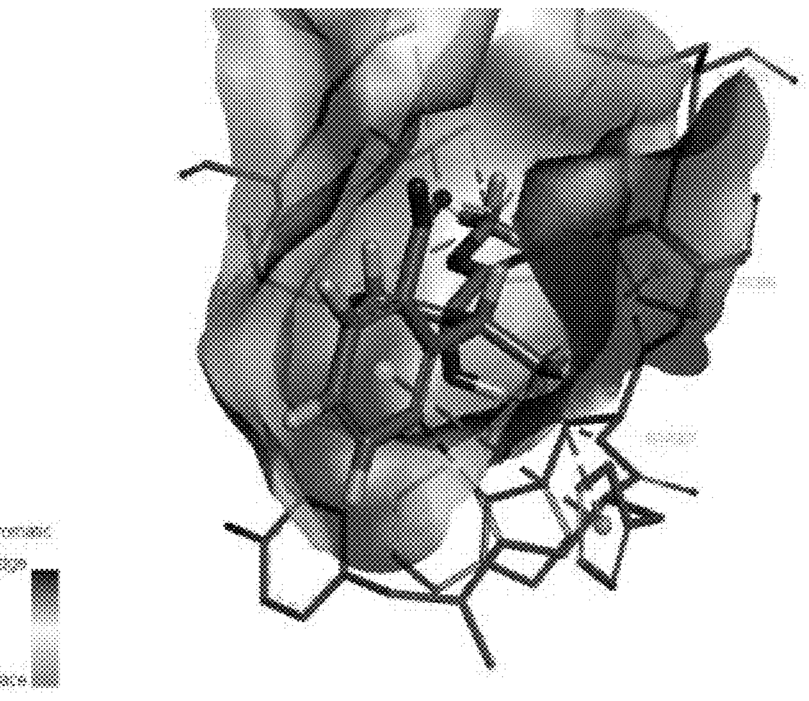
FIGS. 11A-B show a docking result of the nicotinic acid derivative A with 3KKV.
Figure 11B:
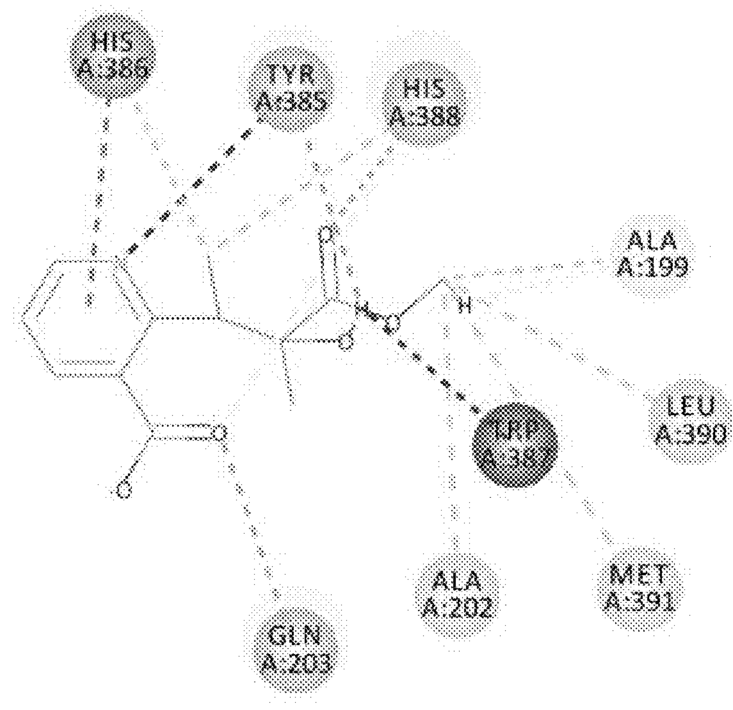
Figure 12A:
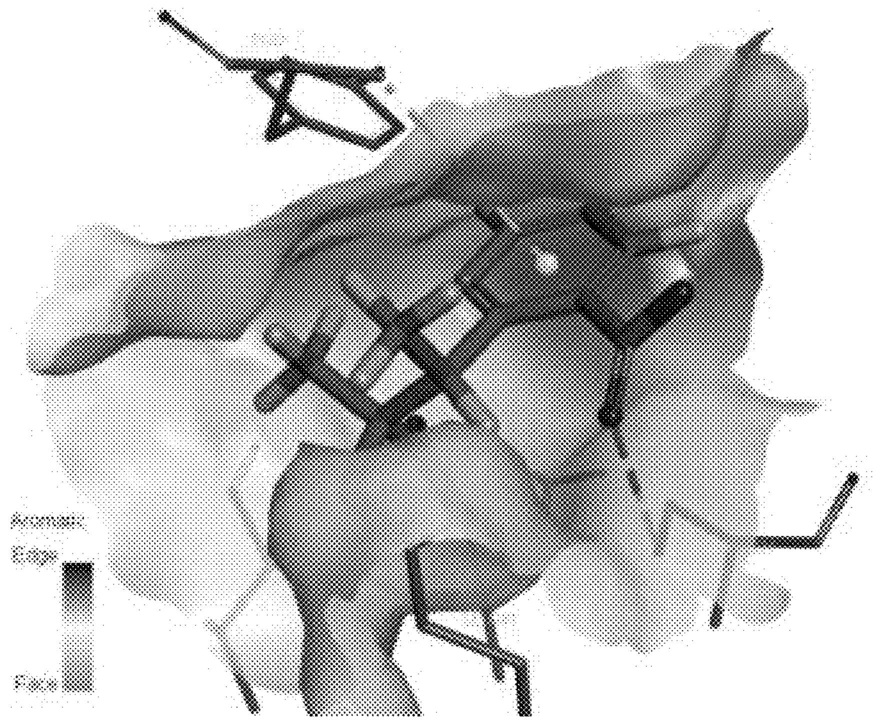
FIGS. 12A-B show a docking result of the nicotinic acid derivative A with 5CJF.
Figure 12B:
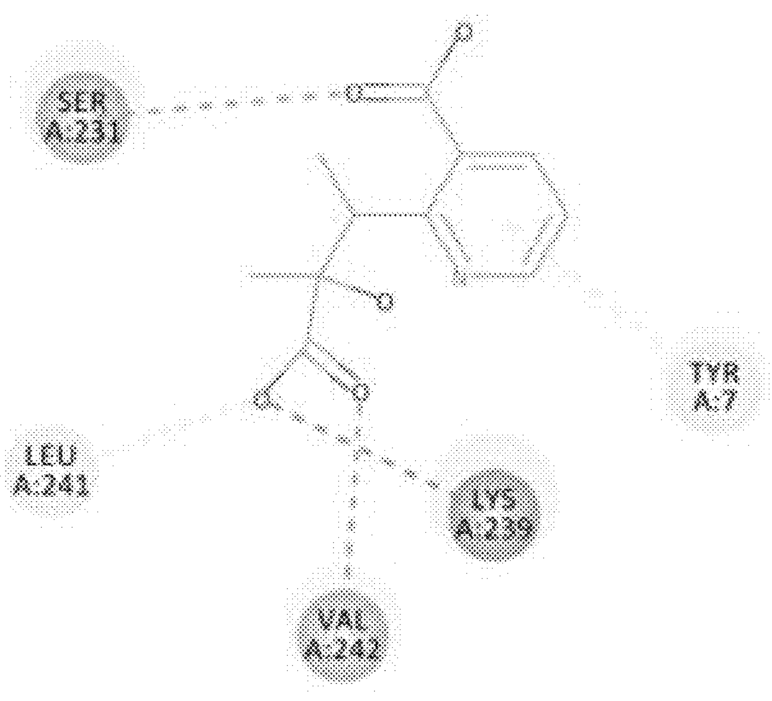
Figure 13A:
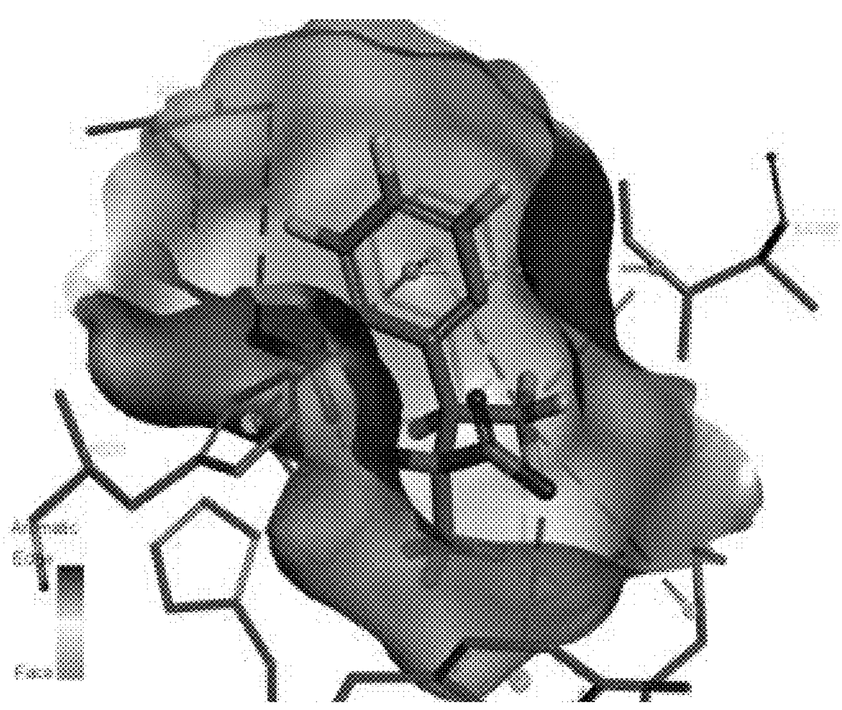
FIGS. 13A-B show a docking result of the nicotinic acid derivative A with 5LYW.
Figure 13B:
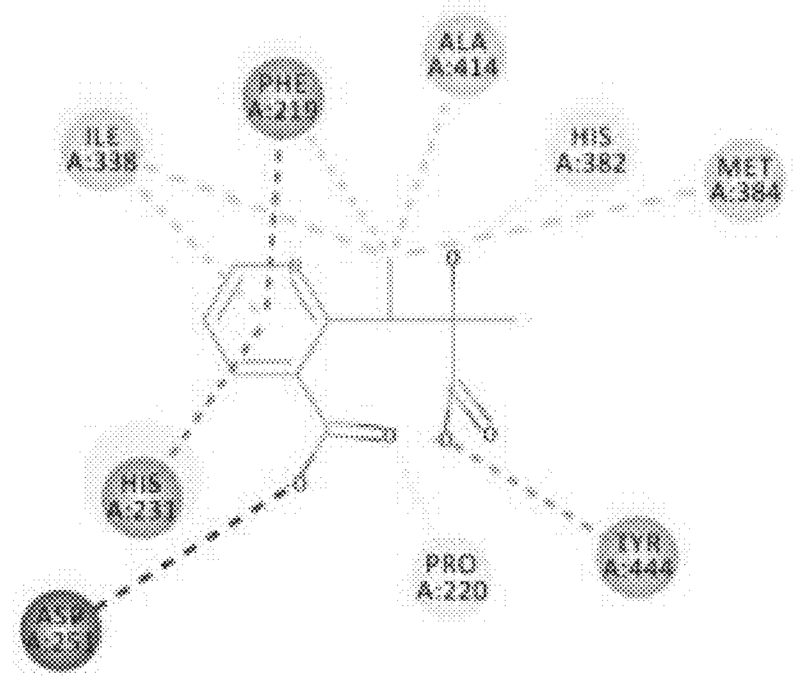
Figure 14A:
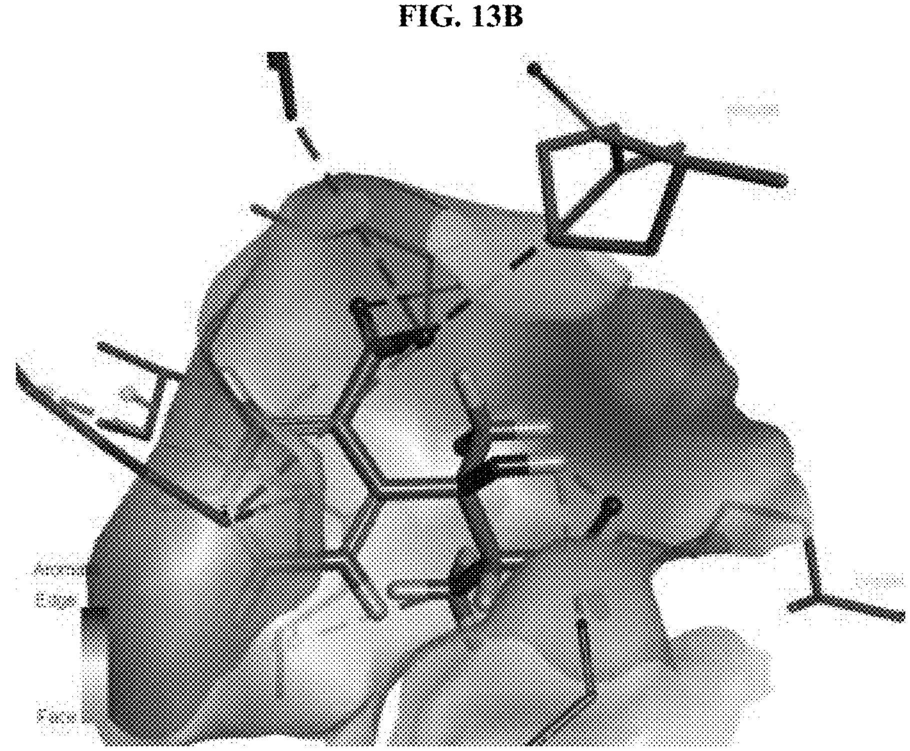
FIGS. 14A-B show a docking result of the nicotinic acid derivative A with 2UZQ.
Figure 14B:
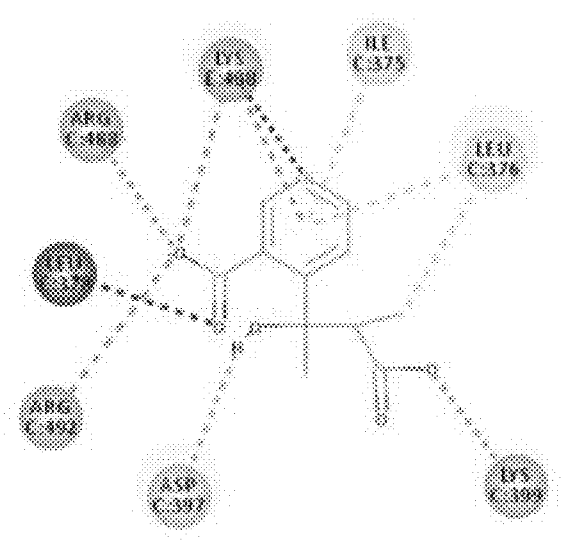
Figure 15A:
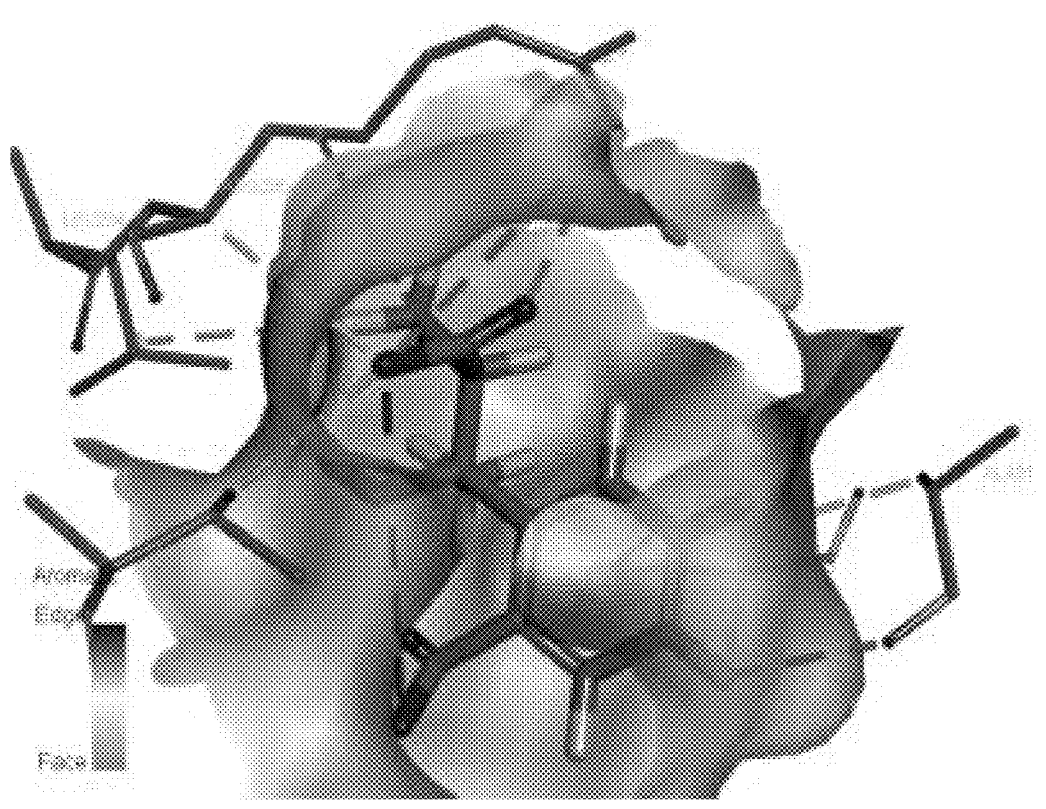
FIGS. 15A-B show a docking result of the nicotinic acid derivative A with 6IIV.
Figure 15B:
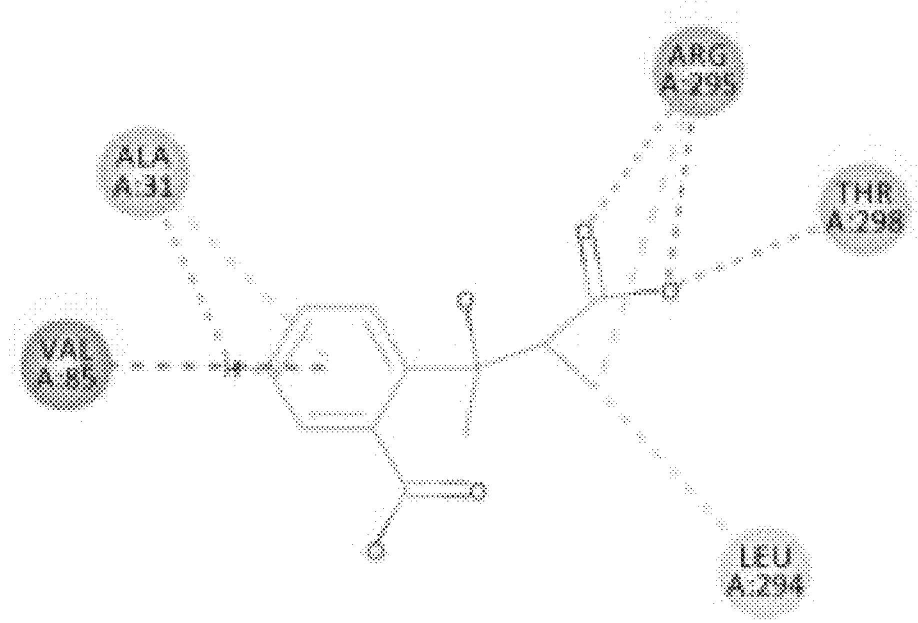

To verify a binding affinity of candidate targets to compounds, simulated molecular docking was implemented in the LibDock program of Discovery Studio 16.1 (DS 16.1). As shown in Table 3, all crystal structures of the candidate targets were directly downloaded from the RCSB protein database (http://www.pdb.org/, updated on June 2020) and checked for resolution. In addition to co-crystallized ligands and structural water molecules, each protein was defined as a receptor, and active sites of the protein were found in a receptor cavity using Discovery Studio tools. Docking protocols were conducted using LibDock to visualize interactions between components and differential proteins in the Discovery Studio. Since LibDock could provide 10 to 100 predicted LibDock scores, and each binding protein had a different position in a protein binding pocket, only the optimal LibDock score was considered. Proteins with the highest scores were considered putative compound targets. The experimental results were shown in FIGS. 11A-B, FIGS. 12A-B, FIGS. 13A-B, FIGS. 14A-B, and FIGS. 15A-B.

TABLE 3

Analysis of target reverse docking of nicotinic acid derivative A

| Uniprot_ID | Protein | Prob | Target |
|---|---|---|---|
| P05979 | Prostaglandin G/H synthase 1 | 0.999 | 6Y3C |
| P21731 | Thromboxane A2 receptor | 0.989 | 6IIV |
| P50579 | Methionine aminopeptidase 2 | 0.915 | 5LYW |
| Q9ULX7 | M-phase inducer phosphatase 2 | 0.974 | 2UZQ |

What is claimed is:

1. A method for treating an autoimmune disease, comprising administrating or applying a nicotinic acid derivative A with an immunosuppressive activity to a subject in need, wherein the autoimmune disease is rheumatoid arthritis; and the nicotinic acid derivative A has a structural formula as follows:

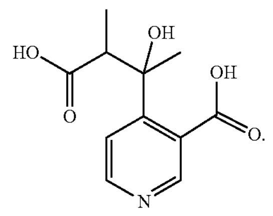 [SMILES: CC(C(=O)O)C(C)(O)c1ccncc1C(=O)O]

* * * * *